United States Patent
Kettinger et al.

(10) Patent No.: US 11,231,473 B2
(45) Date of Patent: Jan. 25, 2022

(54) SIMULTANEOUS MULTI-SLICE (SMS) ACQUISITION OF MEASUREMENT DATA BY MEANS OF MAGNETIC RESONANCE TECHNOLOGY

(71) Applicant: Siemens Healthcare GmbH, Erlangen (DE)

(72) Inventors: Adam Kettinger, Bayern (DE); Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/034,518

(22) Filed: Sep. 28, 2020

(65) Prior Publication Data

US 2021/0096200 A1    Apr. 1, 2021

(30) Foreign Application Priority Data

Sep. 30, 2019 (DE) .......................... 102019214956.1

(51) Int. Cl.
*G01R 33/483* (2006.01)
*G01R 33/54* (2006.01)
(Continued)

(52) U.S. Cl.
CPC .......... *G01R 33/4835* (2013.01); *A61B 5/055* (2013.01); *G01R 33/3607* (2013.01);
(Continued)

(58) Field of Classification Search
None
See application file for complete search history.

(56) References Cited

U.S. PATENT DOCUMENTS

2015/0309142 A1* 10/2015 Li .................. G01R 33/5611
324/309
2021/0096201 A1* 4/2021 Zeller ................. G01R 33/543

OTHER PUBLICATIONS

Breuer et al. "Controlled Aliasing in Parallel Imaging Results in Higher Acceleration (CAIPIRINHA) for Multi-Slice Imaging," Magnetic Resonance in Medicine 53, 2005, pp. 684-691, and the blipped CAIPIRINHA technique, as described by Setsompop et al. in "Blipped-Controlled Aliasing in Parallel Imaging for Simultaneous Multislice Echo Planar Imaging With Reduced gFactor Penalty," Magnetic Resonance in Medicine 67, 2012, pp. 1210-1224.

(Continued)

*Primary Examiner* — Rodney E Fuller
(74) *Attorney, Agent, or Firm* — Schiff Hardin LLP

(57) ABSTRACT

Techniques are disclosed for an improved acquisition of measurement data of an object under examination by means of a magnetic resonance system using a simultaneous multi-slice (SMS) method in which magnetic resonance signals are acquired in at least two slice groups from different slices of the object under examination. The slices contained in a slice group are detected simultaneously in an acquisition of MR signals, which includes the generation of one multiband RF pulse for each slice group. A multiband RF pulse is used to simultaneously manipulate spins of the slices contained in each respective slice group such that the signal intensity profiles of the multiband RF pulses differ from one another. By virtue of the multiband RF pulses being generated according to these techniques, step changes in the signal intensity of the produced image data can be prevented.

9 Claims, 4 Drawing Sheets

(51) Int. Cl.
*A61B 5/055* (2006.01)
*G01R 33/36* (2006.01)
*G01R 33/56* (2006.01)

(52) U.S. Cl.
CPC ....... *G01R 33/3614* (2013.01); *G01R 33/543* (2013.01); *G01R 33/5608* (2013.01)

(56) References Cited

OTHER PUBLICATIONS

Setsompop et al. "Blipped-Controlled Aliasing in Parallel Imaging for Simultaneous Multislice Echo Planar Imaging With Reduced gFactor Penalty," Magnetic Resonance in Medicine 67, 2012, pp. 1210-1224.

* cited by examiner

SIMULTANEOUS MULTI-SLICE (SMS) ACQUISITION OF MEASUREMENT DATA BY MEANS OF MAGNETIC RESONANCE TECHNOLOGY

CROSS-REFERENCE TO RELATED APPLICATIONS

The present application claims the benefit of the filing date of German patent application no. DE 10 2019 214 956.1, filed on Sep. 30, 2019, the contents of which are incorporated herein by reference in their entirety.

TECHNICAL FIELD

The present disclosure relates to techniques for an improved simultaneous multi-slice acquisition of measurement data by means of magnetic resonance technology.

BACKGROUND

Magnetic resonance (MR) technology can be used to generate images of the inside of an object under examination. In simple terms, this is done by placing the object under examination in a magnetic resonance device in a comparatively strong static, homogeneous main magnetic field, also called the B0 field, at field strengths of 0.2 tesla to 7 tesla and higher, with the result that the nuclear spins of the object are oriented along the main magnetic field. High frequency excitation pulses (RF pulses) are applied to the object under examination in order to induce nuclear spin resonances. The induced nuclear spin resonances are measured as what is known as k-space data, and this data is used as the basis for reconstructing MR images or obtaining spectroscopic data. Rapidly switched gradient magnetic fields, called gradients for short, are superimposed on the main magnetic field for spatial encoding of the measurement data. A scheme used to specify a succession over time of RF pulses to be applied and gradients to be switched is called a pulse sequence (scheme). The recorded measurement data is digitized and stored as complex numerical values in a k-space matrix. A multidimensional Fourier transform, for example, can be used to reconstruct an associated MR image from the k-space matrix, which is populated with values. The RF pulses are generated by an RF power amplifier (radiofrequency power amplifier or RFPA). The parts of the object under examination in which the nuclear spins are excited to resonance depend on the effective local strength of the magnetic field and the frequency of the RF pulses, because the resonant frequency of the nuclear spins is itself dependent on the local magnetic field strength. Thus, by suitable variation, a specific slice of the object under examination can be excited selectively in a targeted manner.

In what are known as parallel acquisition techniques (ppa), for instance GRAPPA ("GeneRalized Autocalibrating Partially Parallel Acquisition") or SENSE ("SENSitivity Encoding"), in which a plurality of RF coils are used to acquire only an amount of measurement data that is undersampled in k-space according to the Nyquist theorem, are employed, for instance, to shorten the measurement time needed in total for acquiring the measurement data or to increase the resolution. The "missing" measurement data, i.e. measurement data that is not measured but is required for a complete set of measurement data according to Nyquist theorem, is added here on the basis of sensitivity data for the RF coils used, calibration data, and the measured measurement data.

SUMMARY

The desire for ever faster MR acquisitions in the clinical environment has led to a renaissance in methods in which a plurality of images are acquired simultaneously. These methods can be characterized generally as selectively using for the imaging process, at least during part of the measurement, transverse magnetization of at least two slices simultaneously (e.g. multi-slice imaging, slice multiplexing, simultaneous multi-slice (SMS), etc.). In established multi-slice imaging, the signal is acquired from at least two slices alternately, i.e. fully independently from one another, with corresponding longer measurement time.

Known SMS methods are methods, for example, which employ in the slice direction the methods from the aforementioned imaging by means of ppa, in which knowledge about the sensitivity distribution of the receive coils employed in acquiring the measurement data is used as additional information to fill in measurement data that is undersampled according to Nyquist theorem, so as to separate signals acquired from a plurality of slices into signals from the individual slices. These methods include, for example, the CAIPIRINHA technique, as described by Breuer et al. in "Controlled Aliasing in Parallel Imaging Results in Higher Acceleration (CAIPIRINHA) for Multi-Slice Imaging," Magnetic Resonance in Medicine 53, 2005, pages 684-691, and the blipped CAIPIRINHA technique, as described by Setsompop et al. in "Blipped-Controlled Aliasing in Parallel Imaging for Simultaneous Multislice Echo Planar Imaging With Reduced gFactor Penalty," Magnetic Resonance in Medicine 67, 2012, pages 1210-1224, where the g-factor (short for "geometry factor") mentioned in the latter title represents a measure for a separability of the different receive coils used.

Image data generated by means of SMS methods, however, often exhibit striped step-changes in intensity, also known as "banding artifacts."

Thus, an object of the disclosure is to allow improved simultaneous multi-slice acquisition of measurement data by means of magnetic resonance technology without step-changes in the signal intensity of the generated image data.

The object is achieved by a method as claimed in the claims and elsewhere throughout the disclosure for acquiring measurement data from an object under examination by means of magnetic resonance technology, by a magnetic resonance system, by a computer program, and by an electronically readable data carrier.

A method according to the disclosure for improved acquisition of measurement data from an object under examination by means of a magnetic resonance system using a simultaneous multi-slice (SMS) method, in which magnetic resonance (MR) signals are acquired in at least two slice groups (SG1, SG2, SG3, SG4, SG5, SG6) from different slices of the object under examination (U), wherein slices contained in a slice group (SG1, SG2, SG3, SG4, SG5, SG6) are detected simultaneously in an acquisition of MR signals, comprises the steps:

generating one multiband RF pulse for each slice group, which multiband RF pulse can be used to manipulate simultaneously spins of the slices contained in the respective slice group by means of an RF power amplifier of the magnetic resonance system in such a way that the signal intensity profiles of the multiband RF pulses produced each differ from one another;

acquiring MR signals from all the required slice groups using the multiband RF pulses;

separating the MR signals of the slice groups in each case into single-slice MR signals of the individual slices contained in the slice groups;

producing image data for at least one slice contained in a slice group by reconstructing the single-slice MR signals of the slice.

By virtue of the multiband RF pulses being generated according to the disclosure by means of an RF power amplifier in such a way that signal intensity profiles of the produced multiband RF pulses of the different slice groups each differ from one another, step changes in the signal intensity of the produced image data can be effectively prevented.

The disclosure is based on the knowledge that RF power amplifiers used in the daily clinical routine for generating RF pulses have different properties, which have an effect on the generated RF pulses (generation properties). RF power amplifiers in particular have a low-pass filter effect, for instance, as a generation property, which results in higher-frequency frequency components of the generated RF pulse decreasing in amplitude with respect to lower-frequency frequency components. For conventional RF pulses, these low-pass filter effects as a generation property of an RF power amplifier have no impact, or a negligible impact, on the MR signals generated by the RF pulses because of the narrow frequency bands of these RF pulses. In particular, for multiband RF pulses used in SMS methods to be able to manipulate a plurality of slices simultaneously, which pulses normally have a wide frequency band, the result of these low-pass filter effect can be, however, that because of the reduced amplitude caused by the low-pass filter effect, higher-frequency frequency components attain smaller flip angles than frequency components whose amplitudes are not affected by the low-pass filter effect. Hence, also only a lower signal intensity is attained for the smaller flip angles, resulting in a signal intensity profile that reflects a signal intensity attained for a slice position by a respective frequency component, which profile is characteristic of the RF power amplifier.

An attempt to reduce said low-pass filter effect of an RF power amplifier, for instance by restricting the frequency bandwidth or by extending the RF pulse length of the RF pulse to be generated, has a simultaneous negative impact on the character of the entire MR measurement performed using the generated RF pulse. For example, as a result of an increase associated with the aforementioned measures in sensitivity of the MR measurement to inhomogeneities, e.g. in the magnetic fields used, an increase in a minimum echo time required (time between excitation and acquisition of echo signals as measurement data), and blurring of the profiles of a slice manipulated by the RF pulse, one of the effects of which may be an increased incidence of crosstalk artifacts, for instance.

In conventional SMS methods, for simultaneous excitation of different slices contained in a slice group, the spacing between the slices to be excited simultaneously is usually specified first, and then a first RF pulse having a base RF pulse waveform (e.g. having a fixed frequency bandwidth) is specified by specifying a first center frequency, which defines a first of the slices of the slice group. For each additional slice of the slice group, an additional RF pulse is increased by shifting the center frequency of the first RF pulse by, for each additional RF pulse, a frequency step-change corresponding to the specified spacing of the slices. The first RF pulse and the additional RF pulses are combined into a multiband RF excitation pulse, which manipulates all the slices simultaneously.

If it is intended to excite or manipulate slices from other slice groups, for instance slices lying between the slices manipulated by the multiband RF excitation pulse generated initially for a first slice group, then conventionally the multiband RF excitation pulse already generated for the first slice group is modified by shifting the center frequency of this generated multiband RF excitation pulse in such a way that as a result of the global shift of the modified multiband RF excitation pulse, the other required slices of another slice group can be manipulated by the modified multiband RF excitation pulse. If an already-generated multiband RF pulse is modified by a global shift in its center frequency, the modified multiband RF pulse for the slices manipulated by the modified multiband RF pulse has a signal intensity profile that is identical in shape to the originally generated multiband RF pulse.

This is depicted by way of example in FIG. 2, which shows the signal intensity profiles of conventionally-generated multiband RF pulses of different slice groups SG1, SG2, SG3, SG4, SG5, and SG6.

In the diagram of FIG. 2, signal intensities SI are plotted upwards against the slice position n. In the example shown, 24 different slices are divided into six slice groups SG1, SG2, SG3, SG4, SG5, and SG6, each of which comprises four slices, one from each of the position ranges a, b, c and d.

In order to make the signal intensity profiles of the individual slice groups SG1, SG2, SG3, SG4, SG5, and SG6 distinguishable, a different line type is used for each of the slice groups SG1, SG2, SG3, SG4, SG5 and SG6 to plot the signal intensity for a slice position using a multiband RF pulse generated conventionally as described above (see the key on the right). A signal intensity profile of a slice group SG1, SG2, SG3, SG4, SG5, or SG6 thus, in this case, consists of the values of the signal intensity SI attained for each of the slices of that slice group. In the example shown, the signal intensity of a slice drops with the slice position in which the slice lies in each case in such a way that a lower value of the signal intensity SI is attained for each slice position lying further to the right.

It is evident that the signal intensity profile for each of the slice groups SG1, SG2, SG3, SG4, SG5, and SG6 are identical, and therefore each of the slices of the slice groups SG1, SG2, SG3, SG4, SG5 and SG6 that lies in the same position range a, b, c or d respectively has an identical value of the signal intensity SI. For adjacent slices from different position ranges a, b, c, or d, for instance in FIG. 2 the slices where n=6 and n=7, or n=12 and n=13, or n=18 and n=19, this results in abrupt step-changes in the values of the signal intensity SI.

Thus, conventional generation of multiband RF pulses as described above, combined with the generation properties described above of RF power amplifiers, results in the occurrence, in particular for SMS methods, of the aforementioned unwanted step-changes in the signal intensity at adjacent slice positions that have been manipulated using multiband RF pulses from different slice groups.

A magnetic resonance system according to the disclosure comprises a magnet unit, a gradient unit, a radiofrequency unit, and a control unit designed to implement a method according to the disclosure and comprising a multiband RF pulse generator unit.

A computer program according to the disclosure implements a method according to the disclosure in a control unit when it is executed in the control unit.

Said computer program can also be in the form of a computer program product, which can be loaded directly into a memory of a control unit and which comprises program code means in order to perform a method according to the disclosure when the computer program product is executed in the processing unit of the processing system.

An electronically readable data carrier according to the disclosure comprises electronically readable control information stored thereon, which control information comprises at least one computer program according to the disclosure and is designed such that it performs a method according to the disclosure when the data carrier is used in a control facility (e.g. a control computer, a controller, or control circuitry) of a magnetic resonance system.

The advantages and comments described herein with regard to the method aspects apply analogously also to the magnetic resonance system, to the computer program product, and to the electronically readable data carrier.

BRIEF DESCRIPTION OF THE DRAWINGS/FIGURES

Further advantages and details of the present disclosure are presented in the exemplary embodiments described below, and arise with reference to the drawings, where the examples given have no limiting effect on the invention, in which.

DETAILED DESCRIPTION

Figure 1:
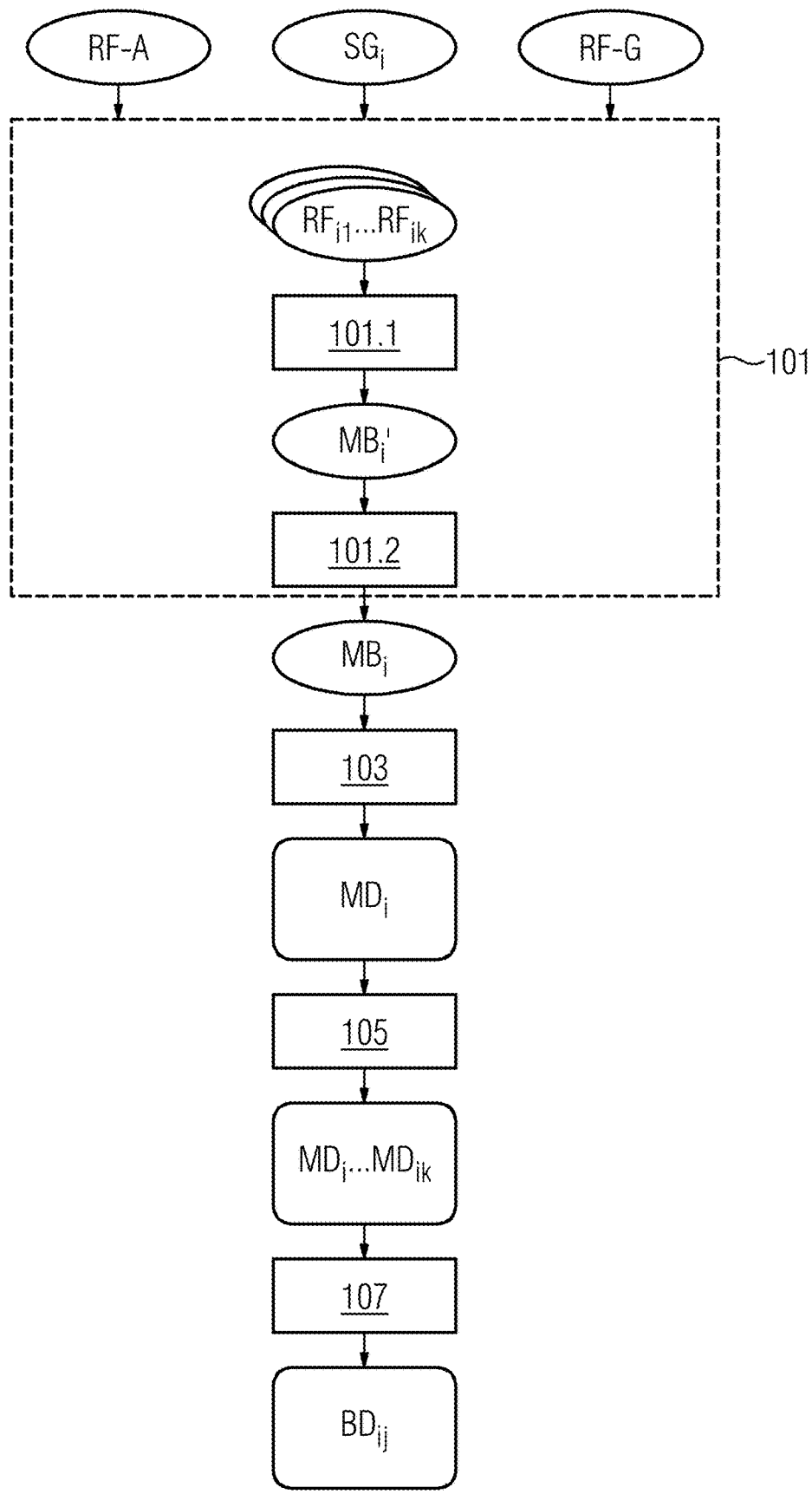
FIG. 1 shows a schematic flow diagram of an example method, in accordance with one or more aspects of the present disclosure.

FIG. 1 is a schematic flow diagram of an example method according to the disclosure for improved acquisition of measurement data from an object under examination by means of a magnetic resonance system using a simultaneous multi-slice (SMS) method, in which magnetic resonance (MR) signals are acquired in at least two slice groups Si (where i=1 to N, N>1) from different slices of the object under examination, wherein slices contained in a slice group Si are detected simultaneously in an acquisition of MR signals. A slice group Si defines the at least two slices contained in the slice group Si and the slice positions thereof.

Aspects include, when generating the multiband RF pulses of the slice groups Si, one multiband RF pulse MBi is generated for each slice group Si by means of an RF power amplifier of the magnetic resonance system in such a way that the signal intensity profiles of the multiband RF pulses MBi produced each differ from one another, and thus an individualized multiband RF pulse MBi is generated for each slice group Si. Spins of the slices contained in the respective slice group Si can be manipulated simultaneously by a generated multiband RF pulse MBi.

The multiband RF pulses MBi can be generated here on the basis of a base RF pulse waveform RF-G, which can be used to manipulate a slice. Here, a base RF pulse waveform may be for example an RF pulse type such as, for instance, a rectangular pulse, a SINC pulse, etc., and, if applicable, may already define a frequency bandwidth of the base RF pulse waveform that can manipulate spins in a desired slice. For given magnetic fields applied by the magnetic resonance system, the position of the manipulated slice in the object under examination can be specified by selecting the center frequency of the base RF pulse waveform. A multiband RF pulse can thus be produced from base RF pulse waveforms having different center frequencies.

A multiband RF pulse MBi of a slice group Si can be produced in each case on the basis of a plan (e.g. predetermined or preset) multiband RF pulse of the slice group, which predetermined multiband RF pulse MBi' is determined on the basis of a number k of base RF pulse waveforms RF-G equal to the number of slices in a slice group Si, wherein the base RF pulse waveforms RFi1 to RFik used to produce the predetermined multiband RF pulse are each assigned a frequency property corresponding to the slices of the slice group, in particular a frequency property, such as the center frequency, that represents the respective slice position, and thus are individualized for the slice group Si. Hence, for each slice group Si, an individualized predetermined multiband RF pulse MBi' is determined, which is composed of individualized base RF pulse waveforms RFi1 to RFik, which each directly have a frequency property corresponding to the slice position of the slices contained in the slice group Si (block 101.1). Said predetermined multiband RF pulse MBi' can now be generated, for example, by an RF power amplifier of the magnetic resonance system (block 101.2). For example, the RF power amplifier of the magnetic resonance system can generate each multiband RF pulse MBi individually (e.g. from an individualized predetermined multiband RF pulse MBi') for the slice group Si. A multiband RF pulse MBi of a slice group Si can thus be generated by the RF power amplifier of the magnetic resonance system generating the respective produced predetermined multiband RF pulse MBi' of the slice group.

It is hence possible to determine individualized base RF pulse waveforms RFi1 to RFik for each slice to be manipulated, whereby generation properties of an RF power amplifier, in particular low-pass filter effects, also influence each of the base RF pulse waveforms RFi1 to RFik, whereby, if no additional factors are taken into account in generating the multiband RF pulses MBi, generation properties of the RF power amplifier have a different effect for each of the multiband RF pulses MBi generated for the different slice groups Si.

Multiband RF pulses MBi generated in this way by means of an RF power amplifier hence reflect, in their signal intensity profiles, properties, in particular the generation properties, of the RF power amplifier.

Figure 3:
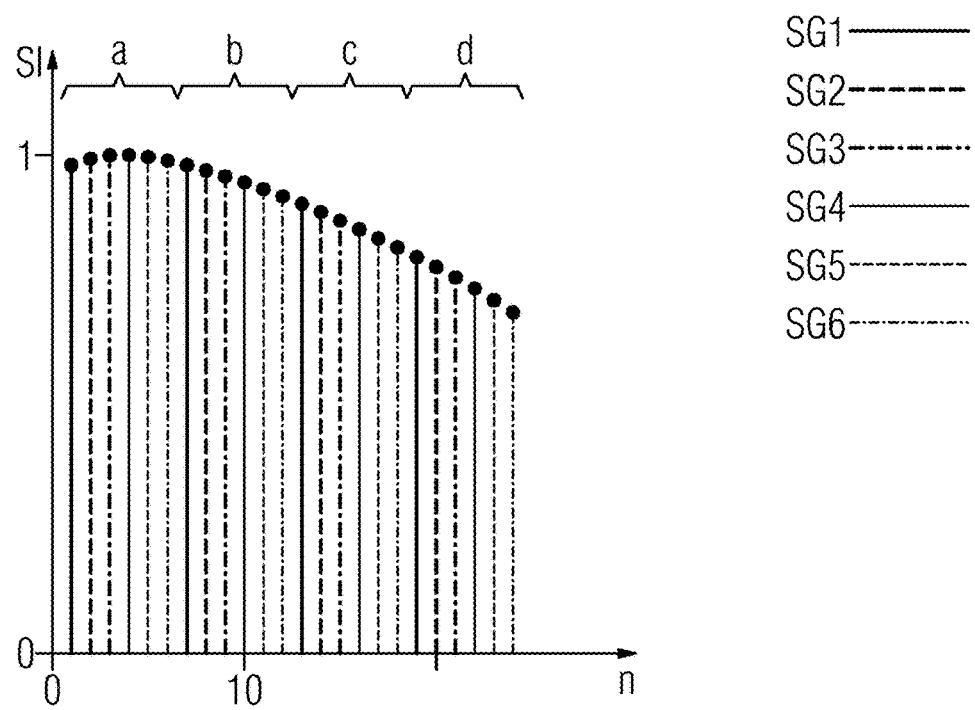
FIGS. 3-4 show diagrams of examples of signal intensity profiles of multiband RF pulses generated for different slice groups, in accordance with one or more aspects of the present disclosure.

FIG. 3 shows an example of signal intensity profiles of individually-generated multiband RF pulses MBi as just described, of six different slice groups SG1, SG2, SG3, SG4, SG5, and SG6.

Figure 2:
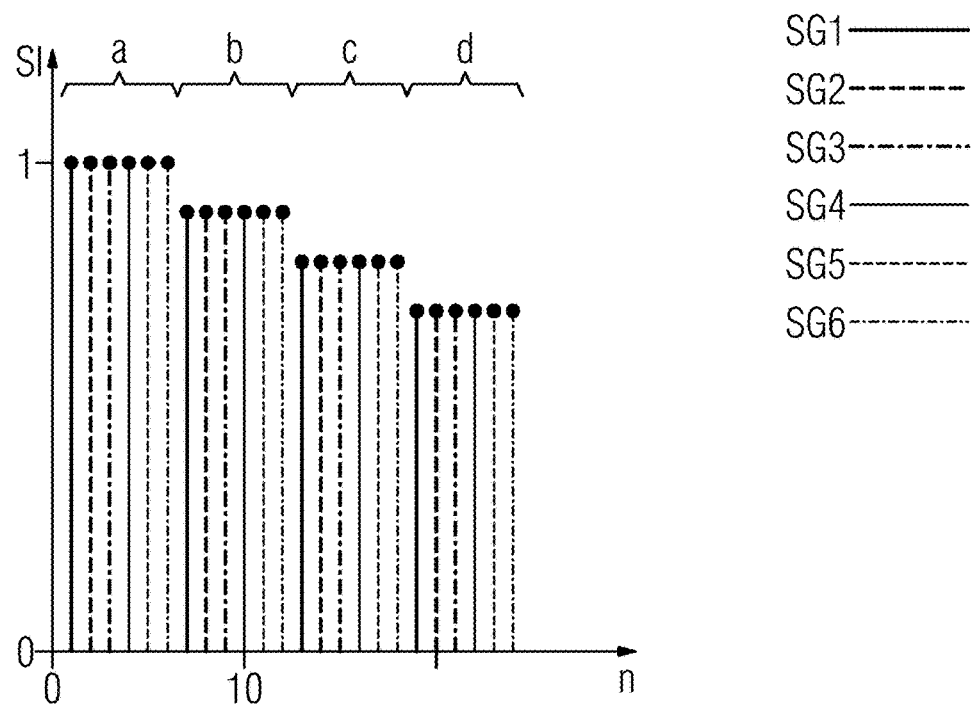
FIG. 2 shows a diagram of an example of signal intensity profiles of conventionally generated multiband RF pulses for different slice groups.

In FIG. 3, relative signal intensities SI of 24 different slices are plotted upwards against their respective slice position n, as was the case in FIG. 2, for easier comparison. The 24 slices are again divided into six slice groups SG1, SG2, SG3, SG4, SG5, and SG6, each of which comprises four slices, one from each of the position ranges a, b, c and d. The progression of the values of the signal intensities SI over the n slices here reflects a low-pass filter effect of an RF power amplifier used to generate the multiband RF pulses of the slice groups SG1, SG2, SG3, SG4, SG5, and SG6.

In order to make the signal intensity profiles of the individual slice groups SG1, SG2, SG3, SG4, SG5, and SG6 distinguishable, the different line types are again used for each of the slice groups SG1, SG2, SG3, SG4, SG5, and SG6 to plot the signal intensity for a slice position (see the key on the right). A signal intensity profile of a slice group SG1, SG2, SG3, SG4, SG5, or SG6 thus in this case again consists of the values of the signal intensity SI attained for each of the slices of that slice group. In the example shown, the signal intensity profile is different for each slice group SG1, SG2, SG3, SG4, SG5, and SG6, and therefore the signal intensity profiles for the slice groups SG1, SG2, SG3, SG4, SG5, and SG6 differ from one another. In this context, the multiband RF pulses for the respective slice groups have been generated such that, although the values of the signal intensities SI for the individual slices vary continuously for adjacent slices, at no point do they arise or drop abruptly for adjacent slices.

It is also conceivable to take into account generation properties of an RF power amplifier when generating multiband RF pulses MBi of slice groups Si in order to influence the signal intensity profiles of the multiband RF pulses MBi.

For this purpose, when producing predetermined multiband RF pulses MBi' from individualized base RF pulse waveforms RFi1 to RFik, pre-emphasis of the individualized base RF pulse waveforms RFi1 to RFik can be performed that affects the individualized base RF pulse waveforms RFi1 to RFik as to compensate for an unwanted generation property, for instance a low-pass filter effect.

Alternatively or additionally, generation properties of an RF power amplifier can be taken into account when generating multiband RF pulses MBi for slice groups Si by constructing e.g. the multiband RF pulses MBi from adapted base RF pulse waveforms, the frequency properties of which are defined such that the generation property of an RF power amplifier has a minimum possible impact on a signal intensity profile of a multiband RF pulse generated from the adjusted base RF pulse waveforms by means of the RF power amplifier, to then generate from a multiband RF pulse generated in this manner from adapted base RF pulse waveforms a multiband RF pulse MBi for a slice group Si by adjusting the frequency property of the multiband RF pulse generated from the adapted base RF pulse waveforms in such a way that the thereby generated multiband RF pulse MBi for a slice group Si can manipulate the slices contained in the slice group Si.

In order to achieve complete compensation for an unwanted effect caused by the generation property by taking into account in this manner generation properties of an RF power amplifier, it would be necessary to know and be able to describe the generation property as precisely as possible. Since this is not normally the case, but rather the generation property can be described only approximately, for instance by a model, then taking account of generation properties of an RF power amplifier in such a way when generating multiband RF pulses MBi for slice groups Si usually manages only to reduce the unwanted effect. Furthermore, this requires knowing or determining the respective generation property for each RF power amplifier used.

Nevertheless, taking into account generation properties of an RF power amplifier when generating multiband RF pulses MBi of slice groups Si can result in a reduction in a variation of the signal intensities in the signal intensity profiles of the multiband RF pulses.

Figure 4:
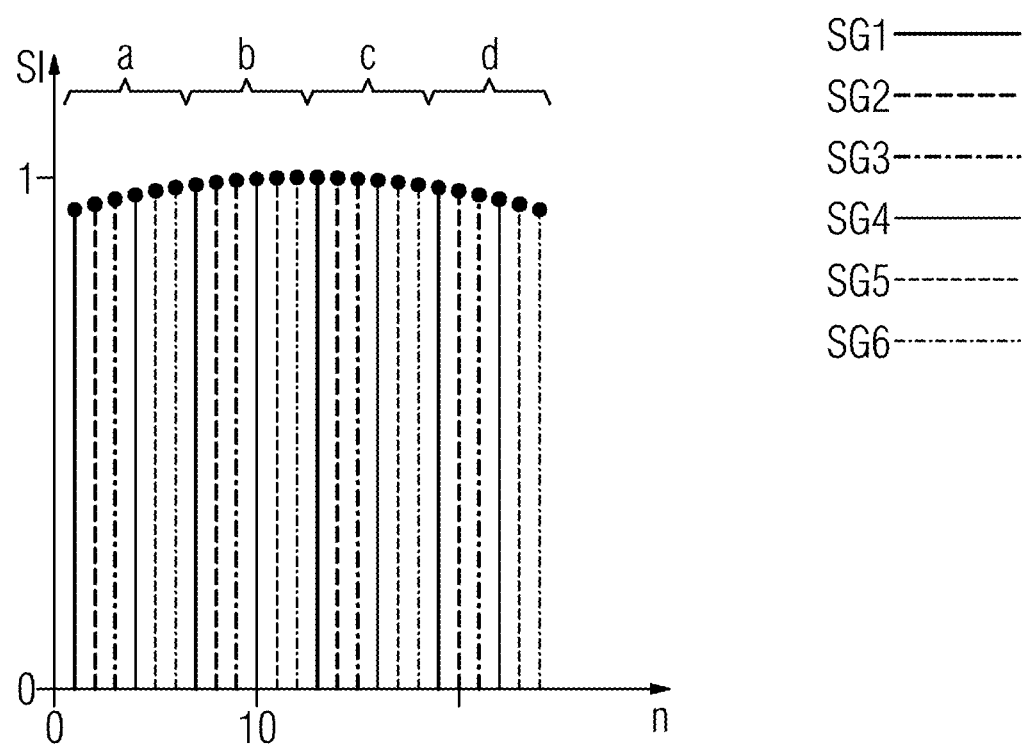

FIG. 4 shows an example of signal intensity profiles of multiband RF pulses MBi of six different slice groups SG1, SG2, SG3, SG4, SG5, and SG6, which pulses are generated individually taking into account generation properties of the RF power amplifier used, as just described.

In FIG. 4, relative signal intensities SI of 24 different slices are plotted upwards against their respective slice position n, as was the case in FIGS. 2 and 3, for easier comparison. The 24 slices are again divided into six slice groups SG1, SG2, SG3, SG4, SG5, and SG6, each of which comprises four slices, one from each of the position ranges a, b, c, and d.

As was the case in FIGS. 2 and 3, different line types are used to plot the signal intensity profiles of the individual slice groups SG1, SG2, SG3, SG4, SG5, and SG6 (see the key on the right). A signal intensity profile of a slice group SG1, SG2, SG3, SG4, SG5, or SG6 thus in this case again consists of the values of the signal intensity SI attained for each of the slices of that slice group. In the example shown, the signal intensity profile is different for each slice group SG1, SG2, SG3, SG4, SG5, and SG6, and therefore the signal intensity profiles for the slice groups SG1, SG2, SG3, SG4, SG5, and SG6 differ from one another. In addition, although taking into account the generation property of the RF power amplifier used still results in continuously varying values of the signal intensity SI for adjacent slices, the progression of the values of the signal intensities SI over the n slices is subject to significantly lower variations in this example than in the example of FIG. 3.

Using the generated multiband RF pulses MBi, it is possible to acquire MR signals MDi from the respective slice groups SGi (block 103).

The acquired MR signals MDi can be separated for each slice group Si into single-slice MR signals MDi1 to MDik of the individual slices contained in the respective slice groups SGi (with k different slices in one slice group SGi) (block 105) in each case. This may take place in a manner typical for SMS techniques.

By reconstructing the single-slice MR signals MDi1 to MDik, it is possible to produce image data BDij (where $1 \leq j \leq k$) for at least one of the k slices contained in the slice group SGi (block 107). This can likewise be performed in a manner typical for SMS techniques. In particular, image data BDij can be created for all the slices contained in the slice group SGi.

By virtue of acquiring, as described here, the MR signals by means of multiband RF pulses MBi generated individually for different slice groups SGi, the image data produced is largely free of fluctuations in the signal intensity.

Produced image data BDij, acquired MR signals MDi and/or separated single-slice MR signals MDi1 to MDik can be stored, for instance for later use, and/or displayed, for instance for a user, on a display device.

Figure 5:
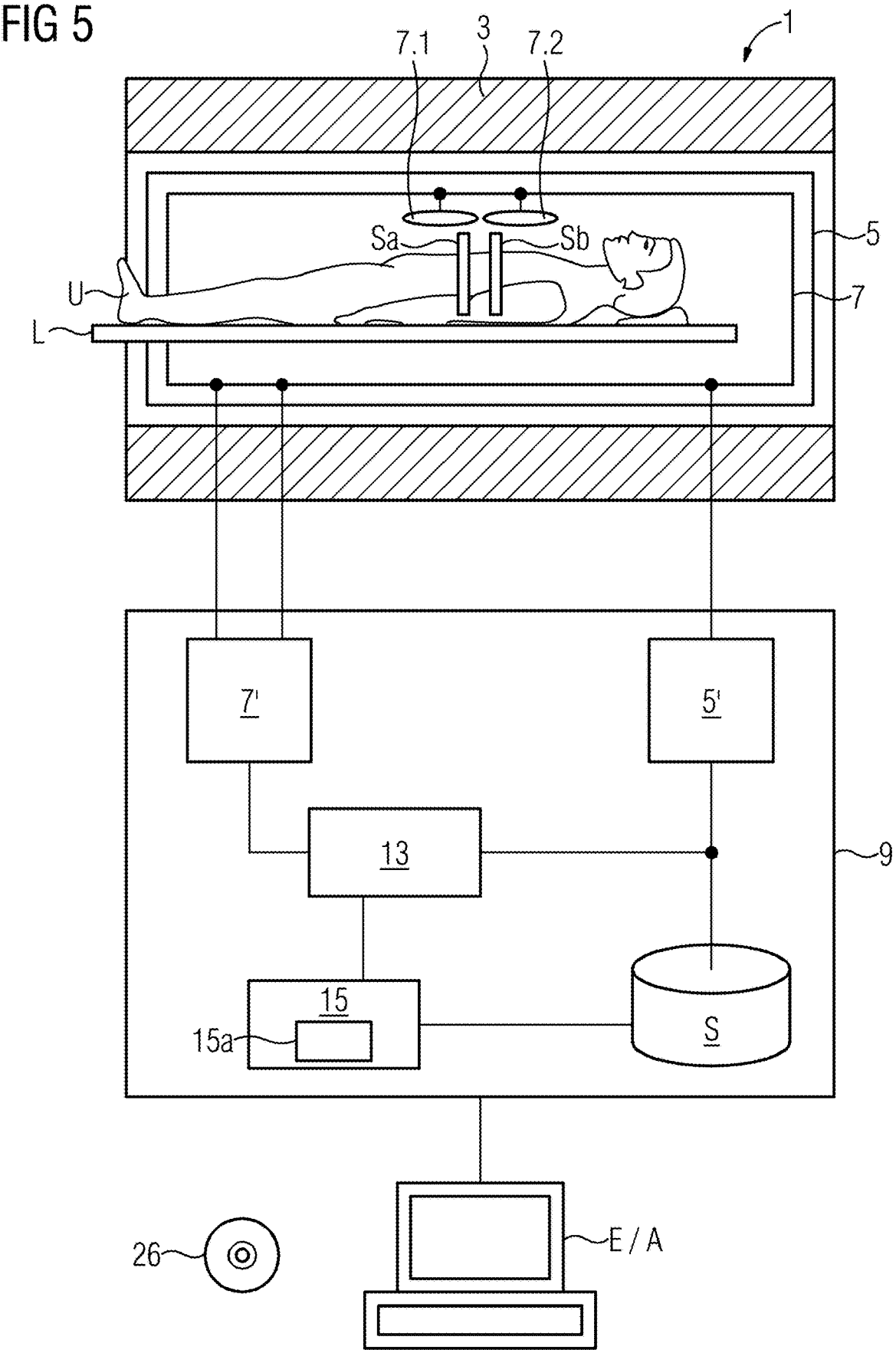
FIG. 5 shows a schematic diagram of an example magnetic resonance system, in accordance with one or more aspects of the present disclosure.

FIG. 5 shows schematically a magnetic resonance system 1 according to the disclosure. This comprises a magnet unit 3 for generating the main magnetic field, a gradient unit 5 for generating the gradient fields, a radiofrequency unit 7 for emitting and receiving radiofrequency signals, and a control unit 9 configured to implement one or more method aspects as described in the present disclosure.

In FIG. 5, these sub-units of the magnetic resonance system 1 are not shown in detail for purpose of brevity. In particular, the radiofrequency unit 7 may include a plurality of sub-units, for instance of a plurality of coils such as the coils 7.1 and 7.2 shown schematically or more coils, which may either be designed solely to transmit radiofrequency signals or solely to receive the induced radiofrequency signals, or be designed to do both.

In order to examine an object under examination U, for example a patient or a phantom, the object can be introduced into the magnetic resonance system 1 into the measurement volume thereof on a couch L. The slices Sa and Sb represent by way of example two different slices Sa and Sb of the object under examination, which slices belong to a slice group and can be detected simultaneously with an acquisition of MR signals.

The control unit 9 is used to control the magnetic resonance system 1 and can control the gradient unit 5 by means of a gradient controller 5', and can control the radiofrequency unit 7 by means of a radiofrequency transmit/receive controller 7'. The radiofrequency unit 7 can here comprise a plurality of channels on which signals can be transmitted or received.

The radiofrequency unit 7, together with its radiofrequency transmit/receive controller 7', is configured to generate and radiate (transmit) an alternating radiofrequency field for manipulating the spins in a region to be manipulated (for instance in slices S to be measured) of the object under examination U. The center frequency of said alternating radiofrequency field, also referred to as the B1 field, as a rule is set so as to lie close to the resonant frequency of the spins to be manipulated. Off-resonance refers to deviations of the resonant frequency from the center frequency. In order to generate the B1 field, currents are applied to the RF coils, which currents are controlled in the radiofrequency unit 7 by the radiofrequency transmit/receive controller 7'.

In addition, the control facility 9 comprises a multiband RF pulse generator unit 15, which comprises an RF power amplifier 15a, and which can be used according to the invention to generate individualized multiband RF pulses for each slice group to be manipulated simultaneously by a multiband RF pulse, which pulses can be implemented by the radiofrequency transmit/receiver controller 7'. The control facility 9 is designed overall to perform a method according to the invention.

A processing unit 13 included as part of the control unit 9 is configured to perform all the processing operations needed for the required measurements and determinations as discussed herein. Intermediate results and results required for this purpose or calculated in this process can be saved in a memory unit S of the control unit 9. The units shown need not necessarily be interpreted here as physically separate units but merely constitute a subdivision into logical units, which, however, can be implemented e.g. in fewer physical units or even in just a single physical unit.

Via an input/output facility E/A of the magnetic resonance system 1 it is possible, e.g. for a user, to direct control commands to the magnetic resonance system and/or to display results from the control unit 9, e.g. results such as image data.

A method described here can also be implemented in the form of a computer program product, such as a non-transitory computer-readable medium that may form part of the control unit 9 (e.g. the memory unit S or the electronically readable data carrier 26) or otherwise accessible by the control unit 9. The non-transitory computer-readable medium may store a computer program and/or executable instructions that, when executed by the control unit 9 or one or more components of the control unit 9, may cause the control unit 9 to perform or otherwise implement the methods as described herein. Likewise, aspects also include the use of the electronically readable data carrier 26, which may comprise electronically readable control information stored thereon, and which information comprises at least one such computer program product as just described and designed to perform the described method when the data carrier 26 is used in the control facility 9 of the magnetic resonance system 1.

The various functional blocks, apparatuses, modules, units, components of physical or functional units, etc., as shown in the drawings and described herein may be implemented unless otherwise noted via any suitable number and type of computer processors, hardware components, the execution of software algorithms, or combinations thereof, and thus may alternatively be referred to as a "unit," "system," "circuitry," or "device."

What is claimed is:

1. A method for acquisition of measurement data from an object under examination using a magnetic resonance (MR) system, comprising:
    generating a plurality of multiband RF pulses, with one multiband RF pulse being generated for each one of at least two slice groups to simultaneously manipulate spins of slices contained in each one of the at least two slice groups to cause the multiband RF pulse associated with at least two slice groups to have a signal intensity profile that differs from one another;
    acquiring, using a simultaneous multi-slice (SMS) technique, MR signals from each one of at least two slice groups from different slices of the object under examination using the plurality of multiband RF pulses;
    separating the MR signals of the at least two slice groups into single-slice MR signals associated with individual slices contained in each one of the at least two the slice groups; and
    producing image data for a slice contained in the at least two slice groups by reconstructing the single-slice MR signals of the respective slice.

2. The method as claimed in claim 1, wherein the multiband RF pulses are generated on the basis of a RF pulse waveform used to manipulate a slice.

3. The method as claimed in claim 1, wherein the act of generating the plurality of RF multiband slices comprises individually generating, via a RF power amplifier of the MR system, each one of the plurality of multiband RF pulses.

4. The method as claimed in claim 1, wherein the act of generating the plurality of RF multiband pulses comprises:
    generating, for each respective slice group of the at least two the slice groups, a predetermined multiband RF pulse that is based upon a number k of base RF pulse waveforms equal to the number of slices in the at least two slice groups, each one of the base RF pulse waveforms having individualized frequency properties corresponding to a respective one of the slices of the at least two slice groups.

5. The method as claimed in claim 1, wherein the act of generating the plurality of RF multiband pulses comprises:
    generating, for each respective slice group of the at least two the slice groups, a predetermined multiband RF pulse via a RF power amplifier.

6. The method as claimed in claim 1, wherein the multiband RF pulse associated with at least two slice groups has a signal intensity profile that is indicative of properties of a RF power amplifier associated with the MR system that is used to generate the multiband RF pulse.

7. The method as claimed in claim 1, wherein the act of generating the plurality of RF multiband pulses comprises:
    generating the plurality of multiband RF pulses using generation properties of a RF power amplifier associated with the MR system that is used to generate the multiband RF pulse.

8. A magnetic resonance (MR) system for acquisition of measurement data from an object under examination, comprising:
    a magnet;

gradient circuitry;
radiofrequency (RF) generation circuitry; and
control circuitry configured to:
- cause the RF generation circuitry to generate a plurality of multiband RF pulses, with one multiband RF pulse being generated for each one of at least two slice groups to simultaneously manipulate spins of slices contained in each one of the at least two slice groups to cause the multiband RF pulse associated with at least two slice groups to have a signal intensity profile that differs from one another;
- acquire, using a simultaneous multi-slice (SMS) technique, MR signals from each one of at least two slice groups from different slices of the object under examination using the plurality of multiband RF pulses;
- separate the MR signals of the at least two slice groups into single-slice MR signals associated with individual slices contained in each one of the at least two the slice groups; and
- produce image data for a slice contained in the at least two slice groups by reconstructing the single-slice MR signals of the respective slice.

9. A non-transitory computer readable medium having instructions stored thereon that, when executed by a controller of a magnetic resonance (MR) system, cause the MR system to:
- generate a plurality of multiband RF pulses, with one multiband RF pulse being generated for each one of at least two slice groups to simultaneously manipulate spins of slices contained in each one of the at least two slice groups to cause the multiband RF pulse associated with at least two slice groups to have a signal intensity profile that differs from one another;
- acquire, using a simultaneous multi-slice (SMS) technique, MR signals from each one of at least two slice groups from different slices of the object under examination using the plurality of multiband RF pulses;
- separate the MR signals of the at least two slice groups into single-slice MR signals associated with individual slices contained in each one of the at least two the slice groups; and
- produce image data for a slice contained in the at least two slice groups by reconstructing the single-slice MR signals of the respective slice.

\* \* \* \* \*